United States Patent
Edwards et al.

(10) Patent No.: US 7,709,268 B1
(45) Date of Patent: May 4, 2010

(54) SAMPLING/DISPENSING DEVICE WITH PLUNGER AND HOUSING SET ONTO PLUNGER

(75) Inventors: Thomas Richard Kerby Edwards, Hauxton (GB); John Cassells, Melbourn (GB); Nicholas Ian Mounteney, Hunting (GB); Gerald Avison, Cambridge (GB)

(73) Assignee: TTP Labtech Limited, Royston, Hertfordshire (GB)

( * ) Notice: Subject to any disclaimer, the term of this patent is extended or adjusted under 35 U.S.C. 154(b) by 1381 days.

(21) Appl. No.: 10/049,488

(22) PCT Filed: Aug. 15, 2000

(86) PCT No.: PCT/GB00/03142

§ 371 (c)(1),
(2), (4) Date: Jul. 22, 2002

(87) PCT Pub. No.: WO01/12329

PCT Pub. Date: Feb. 22, 2001

(30) Foreign Application Priority Data

Aug. 17, 1999 (EP) .................................. 99306463

(51) Int. Cl.
 *B01L 3/02* (2006.01)
(52) U.S. Cl. .................... 436/180; 422/100; 73/864.13; 73/864.16; 73/864.17
(58) Field of Classification Search ................ 156/293, 156/294; 422/100; 604/218; 73/864.11–864.17; 436/180
See application file for complete search history.

(56) References Cited

U.S. PATENT DOCUMENTS

| 3,766,785 | A | | 10/1973 | Smernoff ................... 73/425.6 |
|---|---|---|---|---|
| 3,852,875 | A | * | 12/1974 | McAmis et al. ............ 29/527.4 |
| 3,877,310 | A | * | 4/1975 | Pecsar et al. ............. 73/864.21 |
| 3,882,665 | A | * | 5/1975 | Hughes et al. ................ 57/217 |
| 4,084,730 | A | * | 4/1978 | Franke et al. ............ 73/864.13 |
| 4,121,739 | A | * | 10/1978 | Devaney et al. ............. 222/137 |
| 4,131,112 | A | * | 12/1978 | Kopito et al. ................ 600/578 |
| 4,215,092 | A | * | 7/1980 | Suovaniemi et al. ..... 73/863.32 |
| 4,662,545 | A | * | 5/1987 | Kenney ...................... 222/386 |
| 4,830,832 | A | | 5/1989 | Arpagaus et al. ............. 422/65 |
| 4,967,604 | A | | 11/1990 | Arpagaus et al. ......... 73/864.13 |

(Continued)

FOREIGN PATENT DOCUMENTS

EP 0 226 867 A2 7/1987

(Continued)

OTHER PUBLICATIONS

International Search Report for International Application No. PCT/GB00/03142, Mar. 11, 2000.

*Primary Examiner*—Jan M Ludlow
(74) *Attorney, Agent, or Firm*—Edwards Angell Palmer & Dodge LLP; David G. Conlin, Esq.; Kathryn A. Piffat, Esq.

(57) ABSTRACT

A positive displacement type substance sampling and dispensing device comprises a central plunger formed from a first material. A plunger housing is formed from a second material having a melting point lower than the first material, the housing being formed by molding and setting the second material on to the surface of the plunger so that the plunger can slide in the housing to draw a substance into it.

12 Claims, 6 Drawing Sheets

U.S. PATENT DOCUMENTS 5,658,258 A     8/1997   Kneer et al.  ................. 604/220
6,103,198 A *   8/2000   Brophy et al.  ............... 422/100

FOREIGN PATENT DOCUMENTS

| EP | 0 443 227 A1 | 8/1991 |
| WO | WO 92/20778 | 11/1992 |
| WO | WO 99/34931 | 7/1999 |

* cited by examiner

Figure 7 - Volumetric data for prototype pipettes

Figure 8
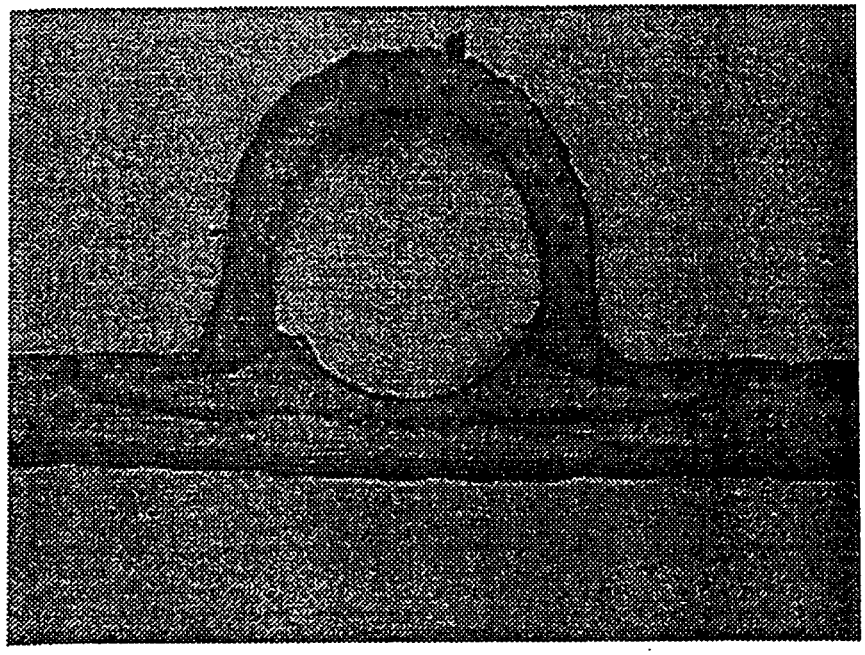
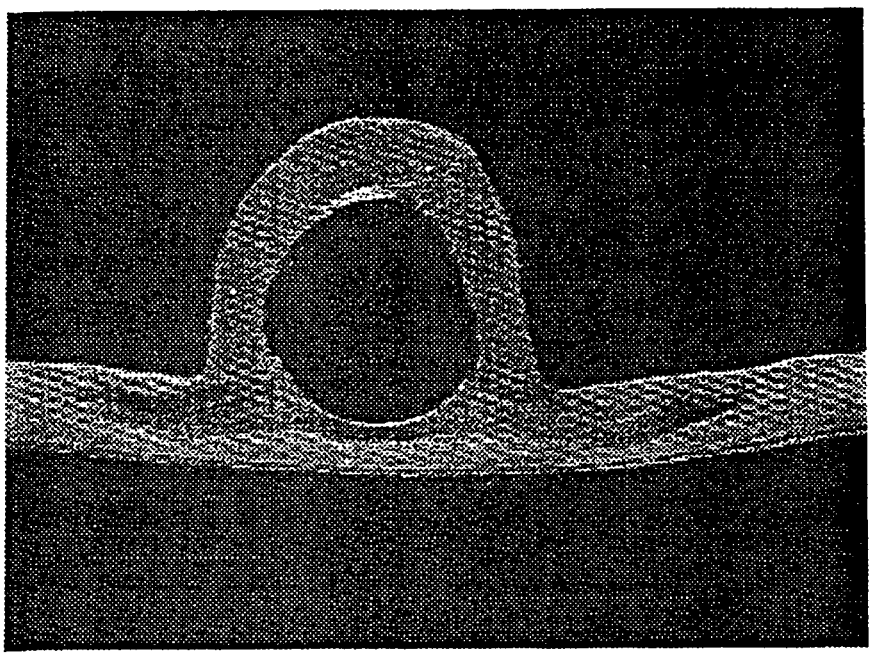

SAMPLING/DISPENSING DEVICE WITH PLUNGER AND HOUSING SET ONTO PLUNGER

This invention relates to a positive displacement type substance sampler/dispenser.

One example of such a dispenser is a plunger-type pipette. Such a pipette is in common usage. It generally comprises an outer cylindrical housing having a central bore in which a plunger sits. The plunger can be slid within the bore to either dispense a substance, such as a fluid or particulate matter, from an orifice in one end of the housing or, if slid in the opposite direction, to draw a fluid or particulate matter into the housing. Such a dispenser has particular benefits in that it can draw up and dispense substances with a high degree of accuracy. Devices in current use do, however, have problems associated with them.

Firstly, it is extremely difficult to produce a device which has a parallel housing bore, meaning that the relationship between the volume of the substance drawn up or dispensed is not linearly relative to the amount of displacement of the plunger. This is particularly true for low volume devices. Furthermore, it is extremely difficult to produce a bore to a level of accuracy which ensures that there is a tight fit between the plunger and the bore wall, meaning that fluid can pass around the edges of the plunger, leading to a reduction in sampling/dispensing accuracy, and leading to a risk of leakage.

The piston is typically slightly oversize for the bore such that it forms an interference fit for sealing. To accommodate this, and to allow for the draft angle on the bore, either the piston or the bore may be made from a compliant material. Examples are medical syringes having rigid polystyrene bores and rubber piston ends, or stiff polypropylene pistons with a compliant thin-walled bore. An alternative sealing arrangement is to provide a lip seal at the end of the piston. These constructions have many disadvantages. In general, compliant materials cannot be used where chemical resistance is required; it becomes increasingly difficult to injection mould bores as the diameter is reduced such that devices capable of accurate dispensing over the nanoliter range are not possible; the need for a draft angle and conventional moulding techniques limits the practical length and thus the dynamic range of the pipette; and the manufacture of pistons with lip seals becomes increasingly difficult as the diameter is reduced below 1 mm.

Thus, present methods of construction are not suited to long bore, high accuracy, low cost and sub-microliter devices.

Other problems associated with such devices includes the fact that they are difficult to handle automatically, their manufacture is costly, and it is often difficult to alter the materials from which the plunger and housing are made without changing moulding tooling for both components.

According to a first aspect of the present invention, there is provided a positive displacement type substance sampling and dispensing device comprising:

a central plunger formed from a first material; and a plunger housing formed from a second material, the housing being formed by moulding and setting the second material on to the surface of the plunger so that the plunger can slide in the housing to draw a substance into it.

The first material may be metal, plastic, ceramic or other suitable material. The plunger may be formed from drawn wire or extruded material to ensure that it has a uniform diameter. The housing may be moulded onto the plunger by injection moulding, welding, coextrusion, casting, dip coating etc.

The materials may be selected such that, preferably, the material of the piston is stiffer and/or has a lower thermal expansion coefficient than the material of the bore. If heat is applied during manufacture, such as using molten plastic to form a bore around a metal wire, the bore will progressively tighten around the piston as the device cools down, thus forming a better seal. If the piston can be maintained at a lower temperature than the material of the bore during forming, it is possible to get further improved sealing because the piston will have expanded even less with respect to the bore. The piston may be actively cooled, or may exploit a higher thermal conductivity or specific heat capacity property than the material of the bore.

During its manufacture, the device may be attached or incorporated into a flexible strip or other backing to which further devices are attached for ease of automated handling.

The flexible strip may have sprocket holes to drive and align the pipettes.

Alternatively, the devices may be manufactured as single discrete pipettes. The pipettes are operated by gripping both the plunger housing and plunger of the pipette and moving the plunger within the bore in the same way as a conventional positive displacement pipette. This operation may be performed by a manual or automatic device. The devices may be used singly or in multiples with or without a backing strip.

The material of the strip may itself form part or all of the housing of the device.

The housing may be formed so that at one end of the device there is provided a frangible tip which can be removed before use to prevent contamination of the device prior to use.

Alternatively, the device may be formed so that it has a heat sealable tip, allowing for the loading of the apparatus with a substance, the substance being sealed in place by sealing of the tip.

The device may also be incorporated into fluidic devices such as "chip-based" analytical devices, chemical synthesizers and sensors to provide a means of forming capillaries, valves and pumps, for example.

The device may have plural plungers arranged on different axes and each sliding within a different region of the housing, the different regions of the housing being joined at a central common core adjacent to an aperture.

By forming the housing around the plunger the cost of manufacture of the device is reduced considerably. Furthermore, such a device has a highly effective seal between the plunger and the housing, and can also be ensured of having a uniform cylindrical wall, even if it is arranged for the dispensing/sampling of very small samples.

The device may be formed by moulding the bore round a drawn wire such that it produces a pipette with a perfectly cylindrical bore throughout. In use, the drawn wire may be projected beyond the tip of the device to pierce the seal of a storage vessel or to act as an ultrasonic probe or electrode for automatic level sensing. A second conductor may be provided parallel to the piston to act as a counter electrode.

The bore may be formed around a piston which has had its tip ground to a shaped point. This provides for an aperture that is a smaller diameter than the bore at the tip of the device, which is important for retaining liquid in larger bore devices.

One example of the present invention will now be described with reference to the accompanying drawings, in which:

FIG. 8 shows photo-micrographs of a cross section of a pipette made by the process of example 1.

Figure 1:
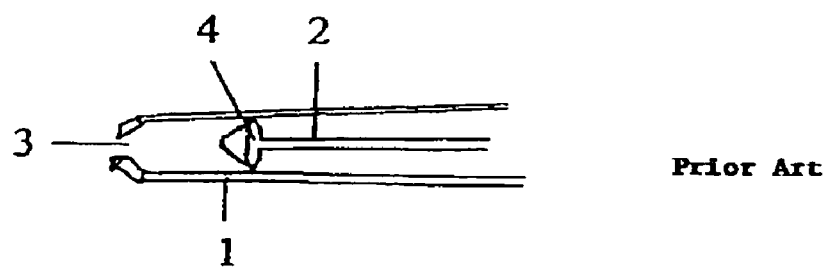
FIG. 1 is a schematic cross-sectional view of a known prior art sampling/dispensing device.

Referring to FIG. 1, a prior art positive displacement-type pipette has an outer housing 1 which has a plunger 2 slidably retained therein. The plunger 2 can be moved to draw a sample into the housing 1 or expel a sample from the housing 1 via an aperture 3. The plunger 2 has a head 4 formed from relatively hard material and which is resilient enough to compensate for a variation in housing diameter with respect to the position of the plunger 2 within the housing. The disadvantages of this device, in terms of difficulty of manufacture, inaccuracies and leakage problems, are discussed above.

Figure 2:
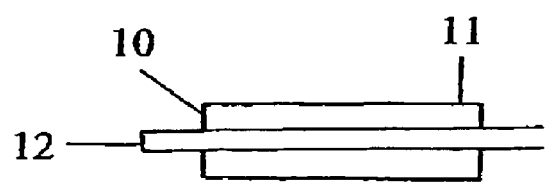
FIG. 2 is a side cross-sectional view of a device according to the present invention during a first stage of manufacture.
Figure 3:
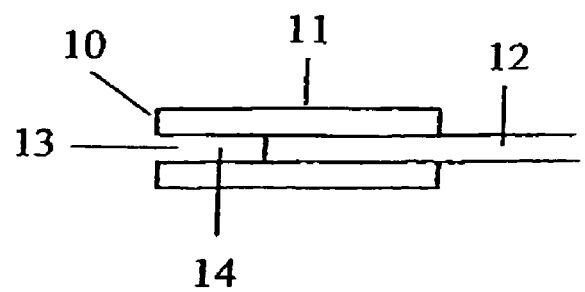
FIG. 3 is a side cross-sectional view of a device according to the present invention after manufacture.

FIG. 2 is a side cross-sectional view of a device 10 in accordance with the present invention during manufacture. The device 10 has a central plunger 12, in this example formed from drawn metal, and an outer housing 11. The outer housing 11 is moulded onto the plunger 12. If a thermoplastic (for example, polyethylene or polypropylene) is used to form the outer housing the plunger should be formed from a material with a higher melting point and preferably lower thermal expansion coefficient than the housing. The plunger, may for example, be made of metal, glass, plastic or ceramic. The housing may also be formed from a thermoset material (for example, silicone rubber or polyurethane resin) or a thermoplastic dissolved in solvent (for example polycarbonate or polyvinylchloride in solvent) in which case the plunger material need not have a higher melting point than the housing. It is preferable to use a thermoset that shrinks on curing.

The housing 11 may be formed by injection moulding, extrusion, or any other well known casting, ultrasonic, welding, dip-coating, co-extrusion, powder coating, thermoforming, spraying forming technique. Once the housing 11 has cooled and set the device can be trimmed to length. In use the plunger 12 can be drawn into the housing, leaving an aperture 13 and an inner core 14 into which a sample can be drawn during use. The inner core 14 is a uniform cylinder as it corresponds to the outer surface of the plunger 12. Furthermore, it is in extremely close engagement with the plunger 12 because of the moulding techniques employed.

Figure 4:
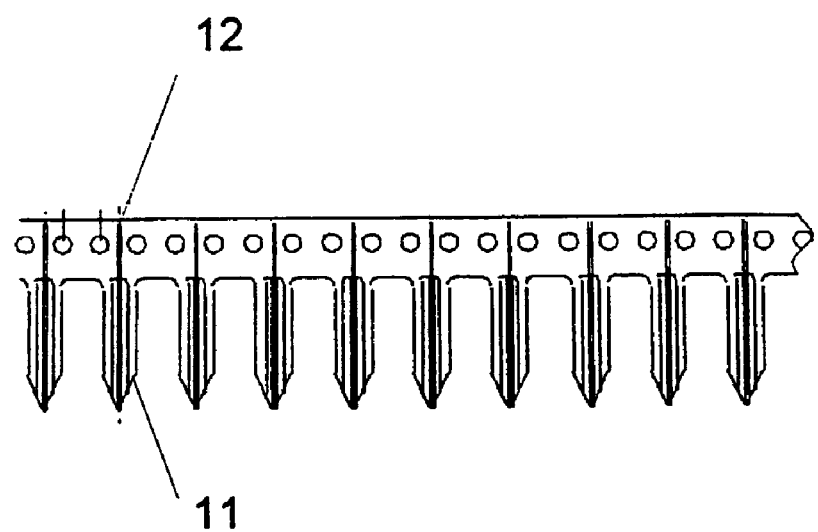
FIG. 4 is a side view of a number of the devices according to the present invention attached to a flexible strip for ease of handling.

FIG. 4 shows how the device 10 of the present invention may be attached to one or more flexible strips 15 for ease of handling. In particular, such an arrangement is handled very easily by automated machinery. In practice, because of the extremely low cost nature of the manufacture of the device 10, it can be treated as a disposable item in use.

Variations of the construction of the device 10 are possible. Firstly, the housing 11 may be formed over the end of the plunger 12 and arranged so that, in use, it has a frangible region which can be snapped off just prior to device use to prevent contamination of the plunger end. Furthermore, the device 10 may be provided with a heat sealable region adjacent to the aperture 13, so that a substance can be placed in the core 14 of the device 10 and sealed therein. This provides a sealed device that, once the end is cropped off, can meter and deliver the contents without loss.

Figure 5:
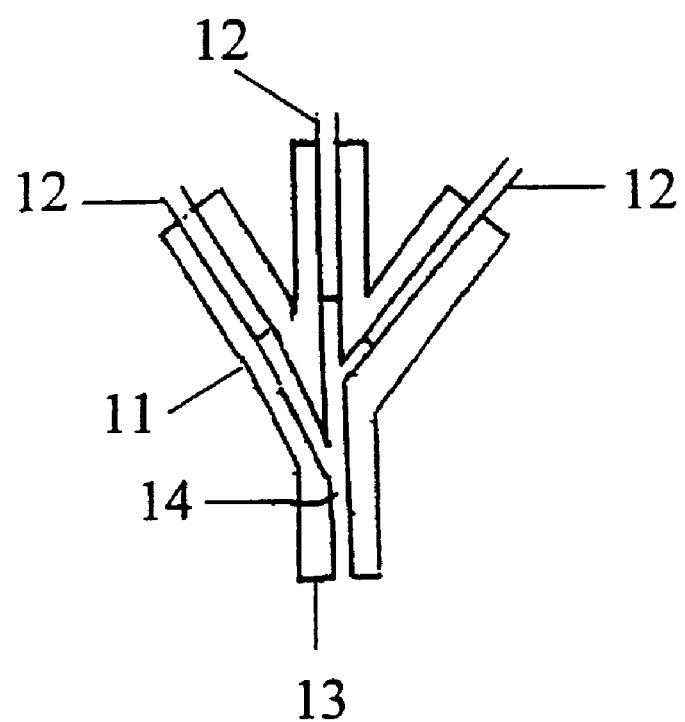
FIG. 5 is a side cross-sectional view of a further example of the present invention.
Figure 6:
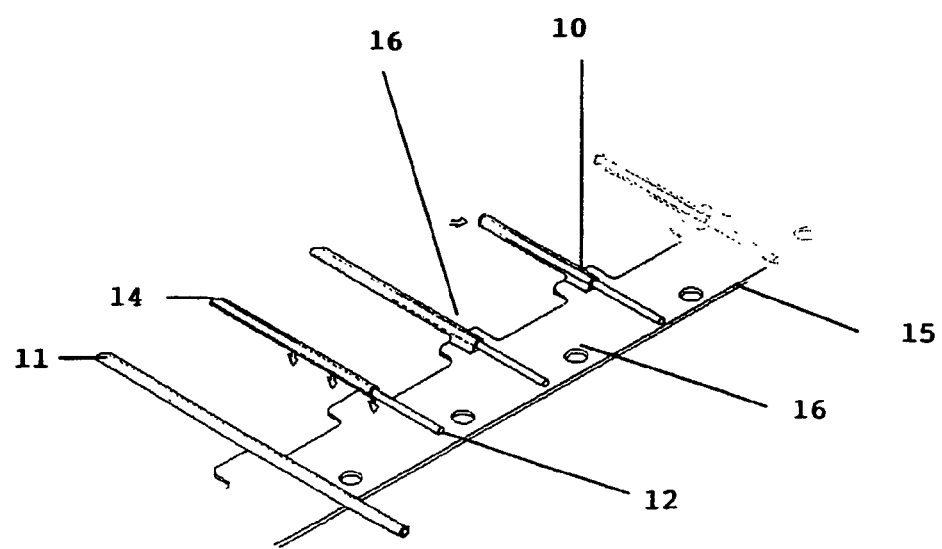
FIG. 6 is a perspective view of a number of the devices according to the present invention attached to a flexible strip.

A further alternative arrangement is shown in FIG. 5. In this arrangement, plural plungers 12 have a outer housing 11 formed thereon. All of the plungers 12 are able to access a common core 14 and tip 13. By withdrawing the pistons, capillary paths are created in the device. Liquid can be drawn up and moved through the system very precisely by moving the pistons. Where capillaries intersect the pistons may be operated as active valves to stop or regulate flow. A viewing window (not shown) may be incorporated into devices to allow the contents to be analysed by a detector. Such an arrangement provides for an extremely cost effective multiple sample withdrawal and dispensing arrangement that still has an high degree of sampling/dispensing accuracy and extremely low leakage.

This type of arrangement is not limited to the simple example shown. A multitude of pumps, capillaries and valves may be incorporated into three dimensional fluidic devices such as "chip-based" analytical devices, chemical synthesisers and sensors using the method of the invention. There are now described three examples which have proved to be particularly advantageous.

EXAMPLE 1

FIG. 4 shows a device constructed according to the present invention. Hard drawn and polished stainless steel wire (British Standard 2056 302S26) of 0.40 mm diameter is inserted into high density polyethylene (HDPE) tubing of 0.43 mm ID and 0.66 mm OD. The tubing length is chosen as 23 mm and the wire length as 30 mm, to leave 7 mm of wire protruding. This tubing is placed across a tape 30 mm wide, made of 0.175 mm polypropylene film. The tubing with wire insert is then welded onto the backing tape using a hemi-cylindrical ultrasonic weld horn along the length of the plastic tube. This applies pressure and melts the plastic tube such that the tube material flows around the wire. This eliminates the 0.03 mm clearance between the wire and the tubing stock. A pipette is thus formed and is simultaneously welded to the backing film in one operation. Multiple pipettes can be formed in a continuous step-and-repeat process.

The tape can then be die-cut to crop the tubing and wire to form the pipette shapes and sprocket holes 16 in one operation.

The backing tape is cut to provide slender pipettes.

Pipettes may be cut from the backing tape and used singly, or may be retained on the backing tape and used in multiples. The backing tape pitch was chosen to be a multiple of 2.25 mm (in this case 4.5 mm) to match the pitch of standard 96, 384 and 1536-well microtitre plates.

Figure 7:
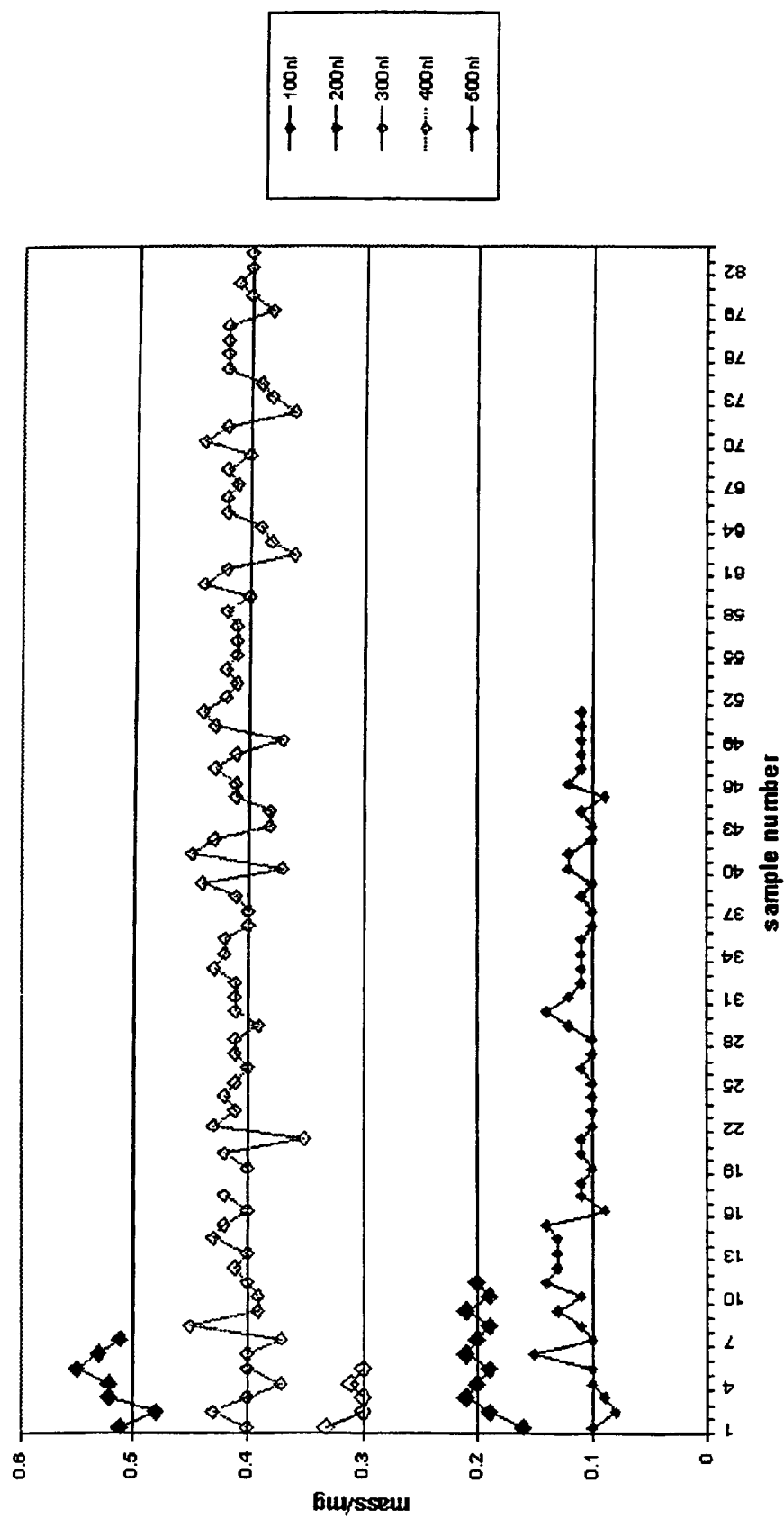
FIG. 7 shows the results of volumetric accuracy trials performed with one example of the present invention.

An aspirate/dispense head can be constructed to grip the backing tape or barrel and pistons independently, and to drive the pistons up and down under user or automatic control to achieve metering(not shown). Volumetric accuracy trials were performed with the prototype device by aspirating 100, 200, 300, 400 and 500 nl samples of writing inks and dispensing them into dry receptacles with tipping off. The results were determined gravimetrically and are shown in FIG. 7. This shows that even non-optimised devices following this invention are capable of accurately aspirating and dispensing samples as small as 100 nl.

Trials with prototype devices of the above construction were carried out to test their performance as storage devices. 100 nl of air was drawn into each device, followed by 100 nl of water and finally another 100 nl of air. Devices were tested with open and sealed ends. The ends were sealed by dipping into hot wax, hot melt glue or by heat welding them closed. Samples were stored for 30 days at room temperature, −20° C.

and −74° C. The open-ended pipettes lost weight rapidly at room temperature, losing all the samples in six hours. All other samples showed no detectable weight loss over the test.

The advantage of this approach for storage is that all of the material stored can be recovered and the storage device can also be used to meter and dispense the stored sample.

FIG. 8 shows a photomicrograph of a cross-section of a pipette made by the process of example 1. The 0.3 mm diameter wire has been withdrawn. The out-of-round distortion was caused by the blade used to cut the section. On re-inserting the wire plunger the device assumes a circular cross-section.

A further device was made by the method above, but using polyethylene-coated PET film for the backing tape. The PET layer provides a stiffer backing tape more suited for mechanical feed.

EXAMPLE 2

A device according to present invention was constructed by insert moulding 0.5 mm diameter stainless steel wire into mould-making grade silicone rubber. A mould was made from three 3 mm thick aluminium sheets sandwiched between two 1 mm thick sheets of glass such that a void 100 mm long, 20 mm high and 3 mm thick was formed. The assembly was held together with spring clips and the top of this void was open to allow filling with resin. An array of stainless steel wires was suspended above the mould with the ends of the wires protruding to the bottom of the mould. Silicone resin was poured into the mould and allowed to cure. Once set, the clips were released and the glass sides taken off the mould to allow the device to be removed. After shaping the pipettes with a knife the wires were cropped to length to form pistons. Operation of the resulting prototype demonstrated suitable function as a pipette.

EXAMPLE 3

A device according to the present invention was constructed by sandwiching stainless steel entomology pins (0.38 mm diameter, 38 mm long, size 00) between polypropylene tapes 0.2 mm thick by 30 mm wide 300 mm long. The pins were laid across one plastics material and the second plastic tape was over-laid to form a sandwich. The plastic sheets were joined together and heat-welded around and along the length of each individual pin between two hemi-cylindrical heated formers. This caused the polypropylene to flow around the pins, thus forming a barrel around each piston. The tape was then cut to form an array of pipettes following the method of Example 1.

EXAMPLE 4

A stiff stainless steel wire of 0.4 mm diameter (EN304, BS1554 or similar) was coated with an extruded polyethylene (PE) sheath to give an overall diameter of 0.80 mm.

Conventional equipment for making insulated electrical wire was used to make the coated wire, but with the process and settings revised to accommodate the wire hardness and the polyethylene coating material. This coated wire was straightened and cut into pipettes of 20 mm length. The coating was stripped off from one end of each pipette to provide a shank 4 mm long. This shank may be gripped to move the plunger in the barrel of the pipette. Conventional electrical wire can be used to make devices of the present invention, but performance is poor because the wire is not stiff enough to allow operation against a tight seal, copper is not desirable as a material in contact with chemical and biological samples, and the PVC coating does not have the desirable properties. The pipette thus formed can be used singly, or preferably is joined transversely to a backing strip.

A backing strip was formed by cutting polyester/Surlyn/EVA film (thickness 125 μm overall) to form a carrier tape with tabs along one edge and sprocket holes for transport (FIG. 4). Pipettes were ultrasonically welded to this carrier tape at 4.5 mm intervals. Strips of pipettes or individual pipettes can be cut off this carrier tape for subsequent use.

The invention claimed is:

1. A method, comprising:
   making a plunger type pipette, by molding and setting a second material around a central plunger having an outer surface and being formed of a first drawn material, such that the second material forms a barrel corresponding to the outer surface of the plunger, and the central plunger can slide in the barrel to draw a substance into it and/or to dispense a substance from it; and
   aspirating a substance into the plunger type pipette by drawing the plunger into the barrel.

2. A method according to claim 1, wherein the first drawn material is drawn wire.

3. A method according to claim 1, wherein the first drawn material is selected from the group consisting of a metal, a ceramic, and a plastic material.

4. A method according to claim 1, wherein the second material is a plastic material.

5. A method according to claim 1, wherein the first drawn material is actively cooled during the molding step.

6. A method according to claim 1, wherein each of the first drawn material and the second material has a thermal conductivity and a specific heat capacity, and wherein a relationship of the thermal conductivities and specific heat capacities of the first drawn material and the second material is selected from the group consisting of:
   (a) the thermal conductivity of the first drawn material is greater than the thermal conductivity of the second material,
   (b) the specific heat capacity of the first drawn material is greater than the specific heat capacity of the second material, and
   (c) the thermal conductivity of the first drawn material is greater than the thermal conductivity of the second material, and the specific heat capacity of the first drawn material is greater than the specific heat capacity of the second material.

7. A method according to claim 1, wherein the molding step comprises performing one of the steps from the group consisting of injection molding, welding, coextrusion casting and dip coating.

8. A method according to claim 1, wherein the barrel, as formed, has a uniform cylindrical shape.

9. A method according to claim 1, wherein the plunger type pipette is attached to a flexible strip in a manner to allow for attachment of a plurality of additional plunger type pipettes.

10. A method according to claim 9, wherein the strip includes a plurality of sprocket holes defined therein to drive and align any attached plunger type pipette.

11. A method according to claim 1, wherein the plunger type pipette is formed to include a heat sealable tip.

12. A method according to claim 1, including the further step of dispensing the substance from the plunger type pipette by propelling the plunger partially or fully through the barrel.

* * * * *